United States Patent
Tonelli et al.

(10) Patent No.: US 9,345,806 B2
(45) Date of Patent: May 24, 2016

(54) MANUFACTURE OF MEDICAL IMPLANTS

(75) Inventors: Claudio Tonelli, Sesto San Giovanni (IT); Piero Gavezotti, Milan (IT); Ritalba Lamendola, Milan (IT)

(73) Assignee: SOLVAY SOLEXIS S.P.A., Bollate (IT)

( * ) Notice: Subject to any disclaimer, the term of this patent is extended or adjusted under 35 U.S.C. 154(b) by 841 days.

(21) Appl. No.: 12/303,348

(22) PCT Filed: Jun. 7, 2007

(86) PCT No.: PCT/EP2007/055626
§ 371 (c)(1),
(2), (4) Date: Feb. 4, 2009

(87) PCT Pub. No.: WO2007/141317
PCT Pub. Date: Dec. 13, 2007

(65) Prior Publication Data
US 2010/0227983 A1 Sep. 9, 2010

(30) Foreign Application Priority Data

Jun. 8, 2006 (EP) .................................. 06115114
Jul. 31, 2006 (EP) .................................. 06118204

(51) Int. Cl.
A61L 27/14 (2006.01)
A61L 28/00 (2006.01)
A61L 29/04 (2006.01)
A61L 31/04 (2006.01)

(52) U.S. Cl.
CPC ............ *A61L 27/14* (2013.01); *A61L 28/0026* (2013.01); *A61L 29/049* (2013.01); *A61L 31/04* (2013.01)

(58) Field of Classification Search
CPC ..... A61L 27/14; A61L 31/04; A61L 28/0026; A61L 29/049
USPC ................ 528/401, 65; 525/440.03, 450, 458
See application file for complete search history.

(56) References Cited

U.S. PATENT DOCUMENTS

| | | |
|---|---|---|
| 3,665,041 A | 5/1972 | Sianesi et al. |
| 3,715,378 A | 2/1973 | Sianesi et al. |
| 3,810,874 A | 5/1974 | Mitsch et al. |
| 3,847,978 A | 11/1974 | Sianesi et al. |
| 5,026,814 A | 6/1991 | Re et al. |
| 5,043,410 A | 8/1991 | Re et al. |
| 5,100,992 A * | 3/1992 | Cohn et al. ....................... 528/26 |
| 5,109,103 A | 4/1992 | Re et al. |
| 5,246,588 A | 9/1993 | Tonelli et al. |
| 5,262,057 A | 11/1993 | Tonelli et al. |
| 5,476,910 A | 12/1995 | Turri et al. |
| 5,508,380 A | 4/1996 | Turri et al. |
| 5,910,614 A | 6/1999 | Turri et al. |
| 2006/0009660 A1 * | 1/2006 | Tchistiakov et al. ......... 568/677 |

FOREIGN PATENT DOCUMENTS

| | | |
|---|---|---|
| EP | 359273 A2 * | 3/1990 |
| WO | WO 97/35906 A1 | 10/1997 |
| WO | WO 2005/065324 A2 | 7/2005 |

OTHER PUBLICATIONS

PCT International Search Report mailed Aug. 6, 2007 for International Application No. PCT/EP2007/055626 (3 p.).
Ratner, Buddy D.. Comprehensive Polymer Science. Edited by Aggarwal, Sundar L.. Ohio (USA): Pergamon Press, 1989. p. vol. 7, Ch. 7, p. 201-247 (47 p.).
Sbarbati Del Guerra, R., et al. In vitro biocompatibility of fluorinated polyurethanes. Journal of Materials Science: Materials in Medicine. 1994, vol. 5, p. 452-456 (5 p.).
Turri, Stefano, et al. NMR of Perfluoropolyether Diols and Their Acetal Copolymers. Macromolecules. 1995, vol. 28, p. 7271-7275 (5 p.).

* cited by examiner

*Primary Examiner* — Nicole M Buie-Hatcher
(74) *Attorney, Agent, or Firm* — Arent Fox LLP

(57) ABSTRACT

The invention pertains to a process for the manufacture cola medical implant, said process comprising:
reacting a mixture of non functional, monofunctional, and bifunctional perfluoropolyethers comprising hydroxyl terminal groups, wherein the average functionality is of at least 1.97 [mixture (M)] with suitable reactants for producing a thermoplastic elastomer;
moulding the so-obtained thermoplastic elastomer for yielding at least a part of the medical implant.
It has been surprisingly found that by using a mixture of perfluoropolyethers having high functionality, it is advantageously possible to manufacture, by moulding thermoplastic elastomers therefrom, medical implants which exhibit improved biocompatibility and which are submitted to reduced chemicals extraction by biological fluids.

15 Claims, No Drawings

MANUFACTURE OF MEDICAL IMPLANTS

CROSS-REFERENCE TO RELATED APPLICATIONS

This application is a U.S. national stage application under 35 U.S.C. §371 of International Application No. PCT/EP2007/055626, filed Jun. 7, 2007, which claims priority of Europeans Application No. 06115114.8, filed Jun. 8, 2006 and European Application No. 06118204.4, filed Jul. 31, 2006, all of these applications being incorporated by reference in their entirety for all purposes.

TECHNICAL FIELD

The present invention concerns a process for the manufacture of a medical implant.

BACKGROUND ART

Extensive investigations have been undertaken over many years to find materials that will be biologically and chemically stable towards body fluids. This area of research has become increasingly important with the development of various objects and articles which can be in permanent contact with blood or other fluids, such as artificial organs, vascular grafts, probes, cannulas, catheters and the like.

Among polymer materials described and used in biomedical field mention can be made notably of polystyrenes, polyethylenes, polytetrafluoroethylenes, polyurethanes, polyurethanes-ureas, siliconic-polyurethanes, polyacrylates.

All these materials for being used for manufacturing medical implants shall guarantee some fundamental requirements, such as notably:
- absence of loss or release of soluble members in the living systems (e.g. in the physiological liquids), unless said release is intentional (e.g. controlled release of drugs);
- stability in the living environment with no polymer degradation (e.g. no breach of the polymer chain, no crosslinking, hydrolysis, swelling which can impair mechanical properties of the implant);
- mechanical and physical properties of the materials appropriated for the target function of the medical implant;
- biocompatibility, no thrombogenicity, no cytotoxicity;
- stability against sterilizing conditions.

Currently available biomaterials comply with selected but not with all above mentioned requirements.

It is also known that the introduction of fluorinated segments in the polymer material of the medical implant can bring valuable advantages, increasing, for instance, the stability of said material.

For instance, it has been disclosed that the presence of a fluoroalkyl group increases the stability of a poly(trifluoropropyl)methylsiloxane, polymer used for biomedical applications (Non Patent Citation 0001: RATNER, Buddy D. *Comprehensive Polymer Science*. AGGARWAL, Sundar L. Ohio (USA): Pergamon Press, 1989. p. Vol. 7, Ch. 7, p. 228.).

Polytetrafluoroethylene (PTFE) has been proposed in the past for biomedical applications, thanks to its outstanding inertness, biocompatibility, stability, thus avoiding any risk of chemicals release due to polymer chain degradation. However, provided the non melt-processable nature and the intrinsic stiffness of PTFE, this material is not suitable for providing small diameter blood vessels prostheses or other cardiocirculatory devices which shall have an elastic behaviour similar to that of body circulatory system.

Polymer materials manufactured from fluoropolyoxyalkene compounds have been described in the art for biomedical applications.

Patent Citation 0001: U.S. Pat. No. 5,026,814 (AUSIMONT S.R.L.). Jun. 25, 1991. discloses fluorinated polyurethanes block copolymers, comprising rubber-like blocks consisting of polyoxyperfluoroalkylene chains and rigid blocks comprising short chain hydrogenated or fluorinated aliphatic moieties, said polyurethane being prepared from perfluoropolyethers comprising hydroxyl groups and being suitable for use in the biomedical sector, for the manufacture of artificial organs, artificial blood vessels, membranes, structural materials and the like.

Patent Citation 0002: U.S. Pat. No. 5,043,410 (AUSIMONT S.R.L.). Aug. 27, 1991. discloses fluorinated polyurethane block copolymers, comprising rubber-like blocks consisting of fluorooxyalkylene units and stiff blocks comprising olefinic unsaturation suitable for crosslinking, said polyurethane being prepared from perfluoropolyethers bearing hydroxyl groups and being appropriate for use in the biomedical sector for the manufacture of artificial organs, artificial blood vessels and membranes.

In vitro biocompatibility of fluorinated polyurethane has been also investigated; fluorinated polyurethane prepared from, inter alia, perfluoropolyethers bearing hydroxyl groups, have been shown to be non thrombogenic and non cytotoxic (Non Patent Citation 0002: SBARBATI DEL GUERRA, R. In vitro biocompatibility of fluorinated polyurethanes. *Journal of Materials Science: Materials in Medicine,* 1994 vol. 5, p. 452-456.).

Patent Citation 0003: U.S. Pat. No. 5,109,103 (AUSIMONT S.P.A.). Apr. 28, 1992. discloses a process for manufacturing polyesters comprising polyoxyfluoroalkylene blocks by polycondensation of perfluoropolyethers bearing hydroxyl groups with dicarboxylic acids or derivatives thereof, said polyesters being endowed with biocompatibility.

Nevertheless, the Applicant has found that said materials, when used in biomedical applications, might undergo chemical extraction phenomena by body fluids and release phenomena of low molecular weight fluorinated materials might impair their biocompatibility.

There is still a need in the art for a process for the manufacture of a medical implant, yielding biocompatible parts which are non thrombogenic, non citotoxic, and have suitable mechanical properties and which, in addition, do not undergo release of fluorochemicals when contacted with body fluids.

Also, are known in the art fluorinated thermoplastic elastomers obtainable by utilizing perfluoropolyoxyalkylene diols having a functionality of at least 1.97. Thus, Patent Citation 0004: U.S. Pat. No. 5,476,910 (AUSIMONT S.P.A.). Dec. 19, 1995. discloses thermoplastic polyester block copolymers obtained reacting a perfluoropolyoxyalkylene diol with a functionality at least equal to 1.97;

Patent Citation 0005: U.S. Pat. No. 5,508,380 (AUSIMONT S.P.A.). Apr. 16, 1996. discloses fluorinated thermoplastic elastomeric polymers obtained from polycondensation reactions of suitable condensation monomers, comprising, inter alia, perfluoropolyether reactive materials, having an average functionality of at least 1.97. Said materials have not been suggested for the manufacture of medical prostheses.

DISCLOSURE OF INVENTION

The invention pertains to a process for the manufacture of a medical implant, said process comprising:

reacting a mixture of non functional, monofunctional, and bifunctional perfluoropolyethers comprising hydroxyl terminal groups, wherein the average functionality is of at least 1.97 [mixture (M)] with suitable reactants for producing a thermoplastic elastomer;

moulding the so-obtained thermoplastic elastomer for yielding at least a part of the medical implant.

It has been surprisingly found that by using a mixture of perfluoropolyethers having high functionality, it is advantageously possible to manufacture, by moulding thermoplastic elastomers therefrom, medical implants which exhibit improved biocompatibility and which are submitted to reduced chemicals extraction by biological fluids.

To the purposes of the invention, the term medical implant (used as synonymous of prosthesis) is intended to denote an artificial device which is made to replace and act as a missing biological structure.

In some cases, medical implants or prostheses can comprise electronics e.g. artificial pacemaker and cochlear implants. In other cases medical implants can have structural features which nuke them suitable to act as reinforcement or replacement of a missing or defective body part, e.g. a blood vessel replacement implant. Optionally, medical implants can provide effective localized drug delivery. The term "drug" as used herein is intended to mean any compound which has a desired pharmacologic effect. Naturally, the drug is generally compatible with the tissue and can be tolerated in a patient.

Prostheses can be used to replace parts lost by injury (traumatic or chirurgical) or missing from birth (congenital) or to supplement defective body parts.

The medical implant may comprise additional parts which are not obtained by the process of the invention. For instance, it may comprise metal inserts, structural reinforcements, radio-opaque inserts, moving motor-driven assemblies, electronic devices, controlling units and the like. It is essential that at least a part of the medical device is obtained by the process of the invention; preferably this part of the medical device made from the process of the invention is the part which will be in contact with biological tissues when the prosthesis is installed in the human body.

The process of the invention is particularly suitable for manufacturing a medical implant chosen from a blood vessel prosthesis, a cardiac surgery device, an angioplastic device, an intraluminal prosthesis for body passageways other than blood vessels, an infusion therapy device, a haemodialysis implant device, a wound dressing device, an orthopaedic prosthesis.

Blood Vessel Prostheses

The process of the invention can be notably used for manufacturing the blood vessel prostheses.

A blood vessel prosthesis is a medical implant (generally via surgical insertion) for repairing injured or diseased blood vessels.

In particular, blood vessel prostheses obtained by the process of the invention advantageously possess:

improved mechanical properties, which nuke them suitable for miming natural blood vessels behaviour and enabling an adequate blood flow;

oxygen and nourishing principles diffusion capabilities through the walls of the prosthesis towards surrounding tissues, miming normal operations of blood vessels.

Cardiac Surgery Devices

Besides, the process of the invention can be notably used for manufacturing cardiac surgery devices.

Among cardiac surgery devices, mention can be made of mechanical circulatory assist devices, also known as ventricular assist devices, which are devices that are used to support the failing heart, which can not be safely and effectively managed with standard medical therapy. These devices may be used for short-term purposes, allowing the heart to "rest" long enough so that it can recuperate and return to normal, independent function. These devices may also be used for more long-term purposes, such as supporting the heart of patients with severe end-stage heart failure who are waiting for a heart transplant.

Non limitative examples of cardiac assist devices are notably cardiac valves, electrical leads for restoring correct cardiac frequency, left-ventricular assist devices (LVAD), hear massage cup and the like.

Angioplastic Devices

The process of the invention can be also used for manufacturing angioplastic devices, such as artery intraluminal prostheses or stents for percutaneous transluminal angioplasty, balloons, guiding catheter, guidewire and the like.

The stents are currently used in the procedures of Percutaneous Transluminal Angioplasty (PCTA), in the treatment of arteries or others blood vessels affected by occlusions. The stent is usually inserted by a delivery system (e.g., such as a guiding catheter) into a vascular lumen and expanded (either via a balloon on a catheter or guidewire, or through self-expansion) into contact with the diseased portion of the arterial wall to provide mechanical support for the lumen. The positioning of stent in the lumen can be used to treat stenosis by re-opening the lumen that had been partially blocked by the stenosis.

It is also known that restenosis (i.e. renarrowing of a peripheral or coronary artery after trauma to that artery caused by efforts to open a stenosed portion of the artery, such as by balloon dilatation) can still occur with such stents in place. In addition, a stent itself can cause undesirable local thrombosis.

It is another object of the present invention to provide an angioplastic device that provides effective localized drug delivery. For example, the drug can be an anticoagulant, such as heparin, antithrombin compounds, platelet receptor antagonists, anti-thrombin antibodies, anti-platelet receptor antibodies, aspirin, protaglandin inhibitors, platelet inhibitors, or tick antiplatelet peptide. The drug can also be a promoter of vascular cell growth, such as a growth factor receptor antagonists, transcriptional activator or translational promoter. Alternatively, the drug can be an inhibitor of vascular cell growth, such as a growth factor inhibitor, growth factor receptor antagonists, transcriptional repressor or translational repressor, antisense DNA, antisense RNA, replication inhibitor, inhibitory antibodies, antibodies directed against growth factors, and bifunctional molecules. The drug can also be a cholesterol-lowering agent, a vasodilating agent, and agents which interfere with endogenous vasoactive mechanisms. Other examples of drugs can include anti-inflammatory agents, anti-platelet or fibrinolytic agents, anti-neoplastic agents, anti-allergic agents, anti-rejection agents, anti-microbial or anti-bacterial or anti-viral agents, hormones, vasoactive substances, anti-invasive factors, anti-cancer drugs, antibodies and lymphokines, anti-angiogenic agents, radioactive agents and gene therapy drugs, among others. The drug may be loaded as in its/their original commercial form, or together with polymer or protein carriers, to achieve delayed and consistent release.

Intraluminal Prostheses for Body Passageways Other than Blood Vessels

The process of the invention advantageously provides for intraluminal prostheses made to repair or reconstruct body passageways by holding open said passageways other than blood vessels (e.g., esophagus, bile ducts, trachea, intestine, vasculature and urethra, among others) which have been, typically, blocked by cancerous growth or tumors.

Devices for Infusion Therapy

Infusion therapy is the intravenous (IV) administration of medications and nutrition, including fluid replacements, chemotherapy, and antibiotics, as well as blood withdrawal for diagnostic testing.

The process of the invention advantageously provides for devices for infusion therapy, such as vascular access systems, i.e. biomedical systems that allow the repeated and/or extended access to the venous system for administration of drugs and nutrition. Vascular access systems include notably Peripherally Inserted Central Catheters (PICC), Percutaneous Intravenous Catheters, Lumen catheters, Double-Lumen catheters e.g. for infusing material and measuring blood pressure simultaneously, Triple-lumen catheters, e.g. for pressure monitoring, blood sampling and fluids/drugs administration.

Haemodialysis Implant Devices

The haemodialysis is a mechanical process wherein the blood of a patient affected by kidney diseases is treated by dialysis to remove toxic substances or metabolic wastes from the bloodstream.

For the treatments of haemodialysis use is notably made of so-called haemodialysis implant devices, which can be manufactured via the process of the invention, i.e. of catheters which are inserted in the vascular system of the patient for withdrawing blood and making it flow through the dialyser machine, such as notably arterious-venous (AV) shunts (or AV grafts) and tunneled catheters, which can be advantageously manufactured by the process of the invention.

An AV shunt is a flexible connection used for joining an artery and a vein in the human body, generally in arms.

A tunneled catheter is a soft tube that is generally placed in a large vein, usually in the neck, which can be cuffed or non-cuffed. Tunneled catheters generally comprise two openings inside; the former being the so-called arterial opening to draw blood from a vein and out of the human body into the dialysis pathway and the latter being the so-called venous opening allowing cleaned blood to return to the human body.

The process of the invention advantageously provides for haemodialysis devices possessing the mechanical properties assuring easiness in implantation, comfort for the patient and assuring minimization of vein erosion and/or stenosis.

Wound Dressing Devices

The process of the invention advantageously provides for wound dressing devices, such as notably artificial skin layers, semi-permanent protective bandages and the like, used in healing a tissue injury (either full or partial thickness) until scar and tissues formation, including regeneration of dermal blood vessels.

The wound dressing devices provided by the process of the invention possess outstanding permeability of the oxygen, thanks to the embedded perfluoropolyether moiety, which is particularly advantageous for healing processes and avoiding necrosis, and suitable impermeability to bacteria and/or contaminants.

Moreover, the process of the invention provides for wound dressing devices having improved non-stickiness properties, which nuke them particularly advantageous for avoiding undesired adhesion of the injured area tissue to the wound dressing device.

It is another object of the present invention to provide wound dressing devices that provide effective localized drug delivery. For example, the drug can be a pentoxifylline, an antimicrobial, a glyceryl trinitrate derivative, a Calcium antagonist, a systemic corticosteroid, a Zinc derivative, a retinoid, an analgesic.

Orthopaedic Prosthesis

The process of the invention advantageously provides for orthopaedic prosthesis for building and/or repairing and/or improving surface properties of skeletal bones and joints such as, but not limited to ligaments, tendons, cartilage, bones, hip joints, spinal disc orthoprosthesis.

The peculiar properties compromise of the medical implant made by the process of the invention, including outstanding mechanical properties and excellent compatibility with body tissues and fluids with substantially no chemicals release nukes them particularly suitable for the production of orthopaedic prosthesis.

Implantable orthopaedic prostheses, in one form, comprise manufactured replacements for the ends and articulating surfaces of the bones of the skeleton. Such prostheses are generally implanted to repair or reconstruct all or part of an articulating skeletal joint that is functioning abnormally due to disease, trauma or congenital defect. Other forms of implantable orthopaedic prostheses, beyond providing manufactured replacements for the ends and articulating surfaces of the bones of the skeletal joints, also provide manufactured replacements for portions of the bones distant from the articulating surface. These other forms may be used in cases of abnormally extensive atrophy or resorption of bone in the vicinity of the articulating surface or prior implant, or in cases where an extensive amount of bone is to be intentionally resected to treat oncological or other diseases of the bone. Because the natural bony areas to which ligaments, tendons and other soft tissues attach are often lost to such extensive resections of the bone, implantable orthopaedic implants designed for such cases often include means for attaching bone and/or soft tissue directly to the implant. Generally such means also provide an initial mechanical attachment, supplemented by later ingrowth and ongrowth of the bone and soft tissue to the prosthesis.

According to another embodiment of the invention, the orthopaedic prosthesis is an artificial knee (or knee prosthesis). Surgery with implantation of knee prosthesis is often performed when a knee joint has been lacerated by osteoarthritis, by articular rheumatism or as a consequence of a fracture in the knee. Other more rare disorders may also necessitate implantation of a new knee joint.

A knee prosthesis typically consists of three components. The first is a replacement of the degenerated articular surface of the thigh bone (metal). The second component which is placed on the top of the shin bone is typically made of the thermoplastic elastomer manufactured according to the invention and it also has an underlying metal coating to be fastened to the bone. Hereby, the semicircular metal part on the thigh bone will generally slide on the plastic coated component, approximately generally 1 cm thick, on the shin bone. Finally, a minor thermoplastic elastomer coating is often implanted on the inside of the knee cap, towards the knee joint.

Other wise, the orthopaedic prosthesis can be an artificial ligament. Artificial ligaments, e.g. artificial cruciate ligaments can be also made by the process of the invention. If a ligament is torn and causes discomfort in daily activities or in sports, an artificial ligament can be implanted.

The process of the invention is more particularly suitable for manufacturing a medical implant chosen from a blood vessel prosthesis, a cardiac surgery device, an angioplastic device; the medical implants above mentioned, which are generally permanently implanted in the human body, particularly enjoy of the advantageous elastomeric behaviour conferred by the perfluoropolyether mixture (M) used in their manufacture and of the advantageous substantial absence of released fluorochemicals, even during extremely long contact time (several years) with body fluids.

The process of the invention comprises reacting a mixture of non functional, monofunctional, and bifunctional perfluoropolyethers comprising hydroxyl terminal groups, wherein the average functionality is of at least 1.97 [mixture (M)].

Said mixture (M) advantageously consists essentially of perfluoropolyethers complying with formula (I) here below:

$$Z\text{—}O\text{—}R_f\text{—}Y \qquad \text{formula (I)}$$

wherein:

R$_f$ is a fluoropolyoxyalkene chain comprising (preferably consisting essentially of) repeating units R°, said repeating units, randomly distributed along the fluoropolyoxyalkene chain, being chosen among the group consisting of:

(i) —CFXO—, wherein X is F or CF$_3$, (ii) —CF$_2$CFXO—, wherein X is F or CF$_3$, (iii) —CF$_2$CF$_2$CF$_2$O—, (iv) —CF$_2$CF$_2$CF$_2$CF$_2$O—, Z and Y, equal or different each other are, at each occurrence, independently chosen among:

non functional groups (or neutral groups, hereinafter) of formula —CF$_3$, —CF$_2$CF$_3$, —CF$_2$CF$_2$CF$_3$, —(CF$_2$)$_f$—CF$_2$(T$_1$), or —(CF$_2$)$_f$—CF(T$_1$)(T$_2$), wherein f is 0 or 1, T$_1$ and T$_2$, equal or different each other, are at each occurrence independently chosen among Cl, Br and H; and functional hydroxyl groups of formula —CF$_2$CH$_2$—O—(CH$_2$CH$_2$O)$_{s'}$H or —CF$_2$CF$_2$CH$_2$O(CH$_2$CH$_2$O)$_{s''}$H, wherein s' and s", equal or different each other and at each occurrence, are integers from 0 to 5.

Preferably in formula (I) here above, R$_f$ is a fluoropolyoxyalkene chain comprising (preferably consisting essentially of) repeating units R°', said repeating units, randomly distributed along the fluoropolyoxyalkene chain, being chosen among the group consisting of:

(i) —CF$_2$O—, (ii) —CF$_2$CF$_2$O—.

The molar ratio between recurring units of type (ii) and recurring units of type (i) ranges advantageously from 0.1 to 10, preferably from 0.5 to 5.

Should both end-groups Z and Y, as above defined, being chosen among functional hydroxyl groups as above detailed, the perfluoropolyether is defined as bifunctional perfluoropolyether comprising hydroxyl terminal groups (bifunctional PFPE, hereinafter).

Should only one of end-groups Z and Y, as above defined, being chosen among functional hydroxyl groups as above detailed, the other end-group being chosen among neutral groups, as above detailed, the perfluoropolyether is defined as monofunctional perfluoropolyether comprising hydroxyl terminal groups (monofunctional PFPE, hereinafter).

Should both end-groups Z and Y, as above defined, being chosen among neutral groups as above detailed, the perfluoropolyether is defined as non functional perfluoropolyether (non functional PFPE, hereinafter).

To the purposes of the invention it is essential that the average functionality of the mixture (M) is of at least 1.97, wherein the average functionality is defined as:

$$\frac{(2 \times \text{moles of bifunctional } PFPE + 1 \times \text{moles of monofuntional } PFPE)}{(\text{moles of bifunctional } PFPE + \text{moles of monofunctional } PFPE + \text{moles of non functional } PFPE)} \qquad \text{[Math. 0001]}$$

The average functionality of the mixture (M) is of advantageously at least 1.98, preferably of at least 1.985, more preferably of at least 1.99.

It is essential for the average functionality of the mixture (M) to be at least 1.97; should the average functionality be less than 1.97, the thermoplastic elastomers thereof are not suitable for manufacturing medical implants, as they undergo substantial release of fluorinated materials in contacts with body fluids.

Average functionality of the mixture (M) can be determined by $^{19}$F-NMR according to the method described in
Non Patent Citation 0003: TURRI, Stefano. NMR of Perfluoropolyether Diols and Their Acetal Copolymers. *Macromolecules*, 1995 vol. 28, p. 7271-7275.

Mixtures (M) of non-functional, monofunctional and bifunctional perfluoropolyethers comprising hydroxyl terminal groups, having average functionality of at least 1.97 are known in the art.

Mixtures (M) suitable for the purposes of the invention can be notably manufactured by photoinitiated oxidative polymerization (photooxidation reaction) of per(halo)fluoromonomers, as described in
Patent Citation 0006: U.S. Pat. No. 3,715,378 (MONTECATINI EDISON S.P.A.). Feb. 6, 1973.
and
Patent Citation 0007: U.S. Pat. No. 3,665,041 (MONTEDISON SPA). May 23, 1972.

Typically, mixtures of perfluoropolyethers can be obtained by combination of hexafluoropropylene and/or tetrafluoroethylene with oxygen at low temperatures, in general below −40° C., under U.V. irradiation, at a wavelength (λ) of less than 3 000 Å.

Subsequent conversion of end-groups as described in
Patent Citation 0008: U.S. Pat. No. 3,847,978 (MONTEDISON SPA). Nov. 12, 1974.
and in
Patent Citation 0009: U.S. Pat. No. 3,810,874 B (MINNESOTA MINING & MFG). May 14, 1974.
is notably carried out on crude products from photooxidation reaction. Perfluoropolyether mixtures obtained from such processes are generally available in the form of mixtures of non functional, monofunctional and bifunctional PFPEs having an average functionality below 1.97.

Suitable separation processes have been described in the art, like notably those disclosed in
Patent Citation 0010: U.S. Pat. No. 5,262,057 (AUSIMONT S.P.A.). Nov. 16, 1993,
Patent Citation 0011: U.S. Pat. No. 5,910,614 (AUSIMONT S.P.A.). Jun. 8, 1999.
and
Patent Citation 0012: U.S. Pat. No. 5,246,588 (AUSIMONT S.P.A.). Sep. 21, 1993,
which enable separating and/or enriching said mixtures in bifunctional PFPE, so as to obtain a mixture having an average functionality of at least 1.97.

Thus, the mixture (M) is advantageously provided by a process comprising:

contacting a mixture of non functional, monofunctional and bifunctional PFPEs having an average functionality below 1.97 with a stationary phase so as to adsorb said mixture on said stationary phase; and fractionally eluting said mixture from said stationary phase with solvent(s) having suitable polarity properties.

Suitable stationary phases and solvent(s) are those described in above mentioned Patent Citation 0013: U.S. Pat. No. 5,262,057 (AUSIMONT S.P.A.). Nov. 16, 1993.
and
Patent Citation 0014: U.S. Pat. No. 5,246,588 (AUSIMONT S.P.A.). Sep. 21, 1993.
and
Patent Citation 0015: U.S. Pat. No. 5,910,614 (AUSIMONT S.P.A.). Jun. 8, 1999.

Preferably, the mixture (M) complies with formula:

Z'—CF$_2$O(CF$_2$CF$_2$O)$_m$—(CF$_2$O)$_n$—CF$_2$—Y', wherein Z' and Y', equal or different each other, are, at each occurrence, independently chosen among:

neutral groups of formula:
—F, —CF$_3$, —CF$_2$CF$_3$, Cl, —Br, —H, —CF$_2$(T$_1$), or —CF(T$_1$)(T$_2$), wherein T$_1$ and T$_2$, equal or different each other, are at each occurrence independently chosen among Cl, Br and H; and functional hydroxyl groups of formula:
—CH$_2$(OCH$_2$CH$_2$)$_{s'''}$OH, wherein s''' has an average value of 1.0 to 3.0, preferably of about 1.5, m and n are chosen as to have a m/n ratio of 0.5 to 5 and an average molecular weight of the mixture (M) of 400 to 10000, preferably of 500 to 5000.

To the purposes of the invention, the term thermoplastic elastomer is intended to denote a material which is both a thermoplastic and an elastomer, i.e. it is a material which above its melt temperature, exhibits a thermoplastic character that enables it to be shaped into a shaped article and to be re-melted several times and which, within its design temperature range, possesses elastomeric behaviour without crosslinking during fabrication.

The term "elastomers" as used herein is intended to denote, as defined by the ASTM, Special Technical Bulletin, No. 184 standard, materials capable of being stretched, at their operating or design temperature, to twice their intrinsic length and which, once they have been released after holding them under tension for 5 minutes, return to within 10% of their initial length in the same time.

A thermoplastic elastomer is thus a material possessing the elastomeric properties as above defined which can be processed in the melt and cooled to the same state; in view of this, thermoplastic elastomers are generally easy to use in manufacturing, for example, by standard moulding process, e.g. by extrusion and/or injection moulding. Because they can be melted and reused, thermoplastic elastomers are thus distinguishable from thermosets or crosslinked elastomers, which cannot be recycled.

Thermosets elastomers, which are distinguishable from thermoplastic elastomers, undergo irreversible chemical modification upon heating; such chemical modification generally yields crosslinked materials which cannot be recycled because they don't melt, the crosslinking tying all the polymer chains together, nuking it impossible for the material to flow.

For the purposes of the invention, it is essential that the material obtained by reacting the mixture (M) is a thermoplastic elastomer, as these materials advantageously possess suitable mechanical properties which nuke them suitable for being used in the fabrication of medical implant and are advantageously easy to be processed, so as to manufacture said medical implant by fast and economic moulding processes, even in case of complex designs or sophisticated assemblies.

According to a first preferred embodiment of the invention, the thermoplastic elastomer is a polyurethane comprising:
at least one fluorinated soft block comprising a fluoropolyoxyalkene chain (R$_f$), as above described;
at least one stiff block comprising an hydrocarbon chain (R$_{HC}$) having from 2 to 14 carbon atoms, optionally comprising one or more aromatic or cycloaliphatic group; said blocks being linked by urethane moieties of formula (II):

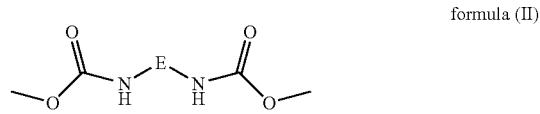

formula (II)

wherein E is a divalent hydrocarbon carbon group, linear or branched, optionally comprising aromatic rings, optionally fluorinated.

Divalent hydrocarbon groups E are notably chosen among:

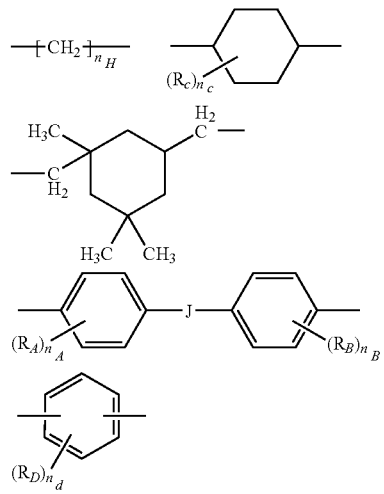

and mixtures thereof;
wherein:
n$_H$ is an integer from 1 to 12, preferably equal to 6;
J is a divalent bridging group chosen among: a single bond; a methylene group (—CH$_2$—); an oxygen atom (—O—); a —C(CH$_3$)$_2$— group; a —C(CF$_3$)$_2$— group; a —SO$_2$— group; a —C(O)— group; preferably J is a methylene group each of R$_A$, R$_B$, R$_C$, R$_D$, equal or different at each occurrence, is independently a halogen atom (e.g. Cl, Br, F), a C$_1$-C$_6$ hydrocarbon group (e.g. methyl, ethyl), a substituent group like notably —OR$_H$, —NR$_H'$R$_H''$, —C(O)—R$_H'''$, wherein R$_H$, R$_H'$, R$_H''$, R$_H'''$, equal or different each other, are independently at each occurrence a hydrogen atom or a C$_1$-C$_6$ hydrocarbon group;

n$_A$, n$_B$, n$_d$, are independently an integer chosen between 0 and 4;

n$_C$ is an integer from 0 to 10.

The process according to the first preferred embodiment of the invention comprises reacting the mixture (M) with at least one diisocyanate of formula OCN-E-NCO, wherein E has the meaning as above defined, and at least one chain extender with a molecular weight of 60 to 450 g/mol chosen among diols of formula HO—$R_{HC}$—OH and/or diamines of formula $H_2N$—$R_{HC}$—$NH_2$, wherein $R_{HC}$ has the meaning as above defined.

Preferably, the chain extended is an aliphatic diol or diamine with 2 to 14 carbon atoms, such as e.g. ethanediol, 1,4-butanediol, 1,6-hexanediol, diethylene glycol, dipropylene glycol and more preferably 1,4-butanediol; or (cyclo) aliphatic diamines such as e.g. isophoronediamine, ethylene diamine, 1,2-propylenediamine, 1,3-propylenediamine, N-methyl-propylene-1,3-diamine, N,N'-dimethylethylenediamine. Most preferred chain extender is 1,4-butanediol.

According to a first variant of this embodiment, the thermoplastic elastomer is a polyurethane further comprising a soft segment comprising a polyoxyalkene chain ($R_{OH}$) of formula (III) and/or (IV) here below:

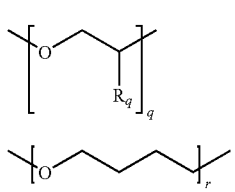

formula (III)

formula (IV)

wherein $R_q$, equal or different at each occurrence, is —H or —$CH_3$; and q and r are, independently, integers from 5 to 250, preferably from 10 to 125.

The process according to this variant of the first preferred embodiment of the invention further comprises reacting with at least one polyether diol of formula HO—$R_{OH}$—OH, wherein $R_{OH}$ has the meaning as above described.

Preferably, the polyether diol is a polytetramethylene diol having an average molecular weight from 500 to 5000.

According to a second variant of this embodiment, the thermoplastic elastomer is a polyurethane further comprising a soft segment comprising a polyester chain chosen among formulae (V) to (VII) here below and mixtures thereof:

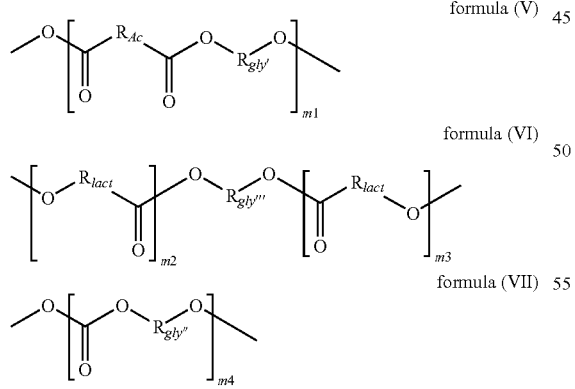

formula (V)

formula (VI)

formula (VII)

wherein:
$R_{Ac}$, equal or different at each occurrence, is independently a divalent $C_1$-$C_{12}$ hydrocarbon group, linear or branched, optionally substituted, optionally comprising one or more aromatic rings; preferably $R_{Ac}$ being a —$(CH_2)_{nAc}$— group, wherein $n_{Ac}$ is an integer from 1 to 6, more preferably $n_{Ac}$=4;

$R_{gly'}$, $R_{gly''}$, $R_{gly'''}$, equal or different at each occurrence, are independently selected among $C_1$-$C_6$ hydrocarbon group, preferably among the following structures: —$(CH_2)_2$—; —$(CH_2)_4$—; —$(CH_2)_6$—; —$CH(CH_3)$—$CH_2$—; —$CH_2$—$C(CH_3)_2$—$CH_2$—;

$R_{lact}$, equal or different at each occurrence, is a $C_2$-$C_{12}$ hydrocarbon group; preferably $R_{lact}$ being a —$(CH_2)_5$— group;

$m_1$, $m_2$, $m_3$, $m_4$ are, independently, integers such as the polyester chain has an average molecular weight of from 500 to 5000, preferably from 500 to 2000.

The process according to this second variant of the first preferred embodiment of the invention further comprises reacting with at least one polyester diol complying with formula (PE-1), (PE-2) or (PE-3) here below, wherein $R_{Ac}$, $R_{gly'}$, $R_{gly''}$, $R_{gly'''}$, $R_{lact}$, $m_1$, $m_2$, $m_3$, $m_4$ have the meaning as above described:

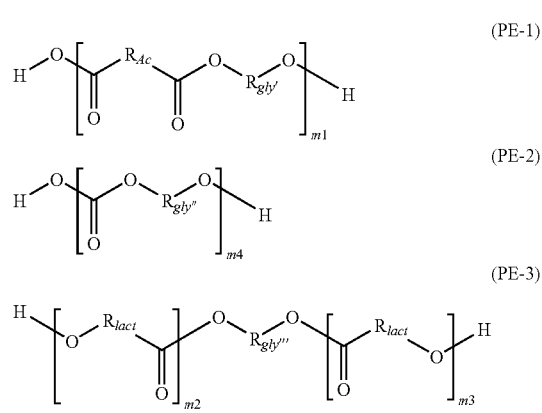

(PE-1)

(PE-2)

(PE-3)

Preferably, the polyester diol is a poly(ε-caprolactone)-diol having average molecular weight of 500 to 5000, preferably of 500 to 2000.

According to a second preferred embodiment of the invention, the thermoplastic elastomer is a polyester comprising:
at least one fluorinated soft block comprising a fluoropolyoxyalkene chain ($R_f$), as above described;
at least one stiff block comprising an hydrocarbon chain ($R_{HC'}$) having from 2 to 16 carbon atoms, optionally comprising one or more aromatic group;
said blocks being linked by ester moieties of formula (VIII):

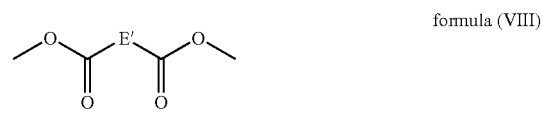

formula (VIII)

wherein E' is a divalent hydrocarbon carbon group, linear or branched, optionally comprising aromatic rings, optionally fluorinated.

Divalent hydrocarbon groups E' are notably chosen among:

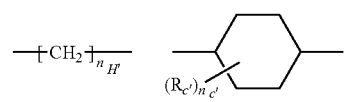

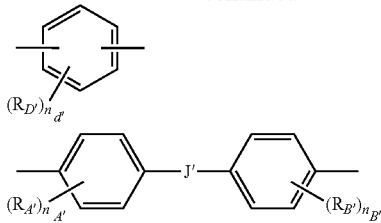

and mixtures thereof;
wherein:
$n_{H'}$ is an integer from 1 to 12, preferably equal to 6;
J' is a divalent bridging group chosen among: a single bond; a methylene group (—CH$_2$—); an oxygen atom (—O—); a —C(CH$_3$)$_2$— group; a —C(CF$_3$)$_2$— group; a —SO$_2$— group; a —C(O)— group;
each of $R_{A'}$, $R_{B'}$, $R_{C'}$, $R_{D'}$, equal or different at each occurrence, is independently a halogen atom (e.g. Cl, Br, F), a C$_1$-C$_6$ hydrocarbon group (e.g. methyl, ethyl), a substituent group like notably —OR$_H$, —C(O)—R$_{H'''}$, wherein R$_H$, R$_{H'}$, R$_{H''}$, R$_{H'''}$, equal or different each other, are independently at each occurrence a hydrogen atom or a C$_1$-C$_6$ hydrocarbon group;
$n_{A'}$, $n_{B'}$, $n_{d'}$, are independently an integer chosen between 0 and 4;
$n_{C'}$, is an integer from 0 to 10.

The process according to the second preferred embodiment of the invention comprises reacting the mixture (M) with at least one diacid of formula HOOC-E'-COOH, wherein E' has the meaning as above defined (or a derivative thereof, such as anhydride, acid halide, ester, amide and the like), and at least one diol of formula HO—R$_{HC'}$—OH, wherein R$_{HC'}$ has the meaning as above defined.

Diacid of formula HOOC-E'-COOH, or the derivatives thereof, can be selected, for instance, from terephthalic acid, isophthalic acid, cyclohexane-1,4-bicarboxylic acid, 4,4'-bicarboxy-diphenylether, 4,4'-bicarboxy-benzophenone, 2,2'-diphenic acid, 4,4'-diphenic acid, adipic acid; sebacic acid; or mixtures and/or derivatives thereof.

Non limitative examples of diols of formula HO—R$_{HC'}$—OH suitable for the process according to the second preferred embodiment of the invention are notably ethanediol, 1,4-butanediol, 1,6-hexanediol, diethylene glycol, dipropylene glycol and more preferably 1,4-butanediol, isopropylidenbiphenol (bisphenol A), hexafluoroisopropylidenbiphenol (bisphenol AF), 4,4'-dihydroxybenzophenone, 4,4'-dihydroxyphenylsulphone, 4,4'-dihydroxydiphenyl, hydroquinone, resorcinol, naphthalen-1,3-diol and isomers thereof, cyclohexane-1,4-diol, decaline-1,5-diol, or mixtures thereof.

Preferably, the hydrocarbon chain R$_{HC'}$ is chosen among the following structures and mixtures thereof:

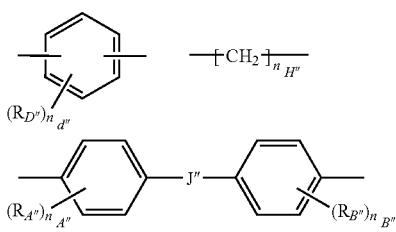

wherein:
$n_{H''}$ is an integer from 1 to 12, preferably equal to 4 or 6, more preferably equal to 4;
J'' is a divalent bridging group chosen among: a single bond; a methylene group (—CH$_2$—); an oxygen atom (—O—); a —C(CH$_3$)$_2$— group; a —C(CF$_3$)$_2$— group; a —SO$_2$— group; a —C(O)— group;
each of $R_{A''}$, $R_{B''}$, $R_{D''}$, equal or different at each occurrence, is independently a halogen atom (e.g. Cl, Br, F), a C$_1$-C$_6$ hydrocarbon group (e.g. methyl, ethyl), a substituent group like notably —OR$_H$, —NR$_{H'}$R$_{H''}$, —C(O)—R$_{H'''}$, wherein R$_H$, R$_{H'}$, R$_{H''}$, R$_{H'''}$, equal or different each other, are independently at each occurrence a hydrogen atom or a C$_1$-C$_6$ hydrocarbon group;
$n_{A''}$, $n_{B''}$, $n_{d''}$, are independently an integer chosen between 0 and 4.

The invention will be described in more detail with reference to the following examples, whose purpose is merely illustrative and not limitative of the scope of the invention.

EXAMPLES

Example 1

Synthesis of a Fluorinated Polyurethanepolyether from Highly Functional Perfluoropolyether (PFPE) Diol In a three necks glass reactor having an inner volume of 100 ml, equipped with a mechanical stirrer and a dropping funnel, under inert atmosphere (nitrogen) were introduced: 15 g of polytetramethyleneglycol (PTMEG, average molecular weight=1000, 15 mmoles) and 7.5 g of 4,4' methylenebis (phenyl isocyanate) (MDI, 30 mmoles).

The temperature was raised to 80° C. by means of external oil bath and reaction mixture was allowed to react for 3 hours.

Then, still at a temperature of 80° C., by means of a dropping funnel, 7 g of a mixture of PFPE compounds comprising hydroxyl groups of structure: Z—CF$_2$O(CF$_2$CF$_2$O)$_m$—(CF$_2$O)$_n$—CF$_2$—Z (Z=CH$_2$OH, average molecular weight=1950, average equivalent weight=980, average functionality=1.99; 3.6 mmoles) were added in 6 hours. The PFPE reagent had been obtained according to the teachings of U.S. Pat. No. 5,262,057, starting from corresponding raw material having average functionality of 1.92.

The reaction mixture was allowed to react for another 3 hours; then 1.03 g of 1,4-butanediol (BDO, 11.4 mmoles) were added. By means of a mechanical pump, the reaction mixture was progressively brought under vacuum under vigorous stirring. The reaction vessel was then brought back to room pressure and viscous reaction mixture was poured in a mould which was then placed in a press at 220° C. for 2 minutes.

The mould was then cooled to 130° C. and maintained at this temperature for 7 hours for completing polymerization.

The mould was finally cooled at room temperature and the moulded slab of polymeric material was kept at room temperature for 2 weeks before characterization tests (mechanical testing and surface characterization) and application runs.

Comparative Example 2

Synthesis of a Fluorinated Polyurethane/Polyether from Low Functionality PFPE Diol Same procedure as described in example 1 was repeated but using 7 g of a mixture of PFPE compounds comprising hydroxyl group complying with formula Z—O—R$_f$—Y, prepared as described in U.S. Pat. No. 5,262,057, having an average molecular weight of 1900, an equivalent weight of 1010 and an average functionality of 1.88 (3.7 mmoles), and 1.0 g (11.1 mmoles) of BDO.

Comparative Example 3

Synthesis of a Hydrogenated Polyurethane/Polyether

Same procedure as described in example 1 was repeated but using as starting materials only PTMEG (15 g, 15 mmoles), MDI (7.5 g, 30 mmoles) and BDO (1.33 g, 14.7 mmoles), with no addition of PFPE compounds comprising hydroxyl groups.

Example 4

Synthesis of a Fluorinated Polyurethane/Polyester from High Functionality PFPE Diol In a three necks glass reactor having an inner volume of 100 ml, equipped with a mechanical stirrer and a dropping funnel, under inert atmosphere (nitrogen) were introduced: 30 g of polycaprolactonediol (PCLG, average molecular weight=2000, 15 mmoles) and 7.5 g of 4,4'-methylene bis (phenyl isocyanate) (MDI, 30 mmoles).

The temperature was then raised to 80° C. by means of external bath oil and the reaction mixture was allowed to react at this temperature for 3 hours.

Still keeping the mixture at 80° C., by means of a dropping funnel, 7 g of a mixture of PFPE compounds comprising hydroxyl group having general formula: $Z-CF_2O(CF_2CF_2O)_m-(CF_2O)_n-CF_2-Z$ ($Z=-CH_2OH$) of average molecular weight=1950, equivalent weight=980, average functionality=1.99; corresponding to 3.6 mmoles. Said PFPE reagent had been obtained according to the teachings of U.S. Pat. No. 5,262,057, starting from corresponding raw material having average functionality of 1.92.

The reaction mixture was allowed to react under inert atmosphere for another 3 hours; then 1.03 g of 1,4-butanediol (BDO, 11.3 mmoles) were added.

The reaction vessel was then brought back to room pressure and viscous reaction mixture was poured in a mould which was then placed in a press at 220° C. for 2 minutes.

The mould was then cooled to 130° C. and maintained at this temperature for 7 hours for completing polymerization.

The mould was finally cooled at room temperature and the moulded slab of polymeric material was kept at room temperature for 2 weeks before characterization tests (mechanical testing and superficial characterization) and application runs.

Comparative Example 5

Synthesis of a Fluorinated Polyurethane/Polyester from Low Functionality PFPE Diol Same procedure as described for example 4 was followed, but using 7 g of a mixture of PFPE compounds comprising hydroxyl group complying with formula $Z-O-R_f-Y$, prepared as described in U.S. Pat. No. 5,262,057, having an average molecular weight of 1900, an equivalent weight of 1010 and an average functionality of 1.88 (3.7 mmoles) and 1.0 g of BDO (11.1 mmoles).

Comparative Example 6

Synthesis of a Hydrogenated Polyurethane/Polyester from Hydrogenated Diol

Same procedure as described for example 4 was followed, but using 30 g of polycaprolactonediol (PCLG, average molecular weight=2000, 15 mmoles), 7.5 g of 4,4'-methylenebis(phenyl isocyanate) (MDI, 30 mmoles) and 1.33 g of 1,4-butanediol (BDO, 14.7 mmoles), with no addition of PFPE compounds comprising hydroxyl groups.

Example 7

Synthesis of a Fluorinated Polyester from High Functionality PFPE Diol 48.5 g of dimethylterephthalate (DMT, 250 mmoles), 36 g of 1,4-butanediol (BDO) (400 mmoles) and $1\times10^{-3}$ mmoles of Titanium tetraisopropylate (5% wt isopropanol solution) were introduced in a three-necked glass vessel having an inner volume of 500 ml, equipped with a mechanical stirrer, a dropping funnel and a distillation column for eliminating volatiles and reaction by-products.

Then 150 g of poly tetramethyleneglycol (PTMEG, average molecular weight=1000, 150 mmoles) and 1 g of IRGANOX® 1098 anti-oxidant were added.

The reaction mixture was then heated via an external oil bath to 200° C. Polymerization was pursued at this temperature under stirring, by venting volatiles (including methanol) via distillation.

After 30 minutes, once all the methanol has been eliminated, 30 gr of a PFPE mixture of formula $Z-CF_2O(CF_2CF_2O)_m-(CF_2O)_n-CF_2-Z$ ($Z=CH_2(OCH_2CH_2)_{n'}OH$, average n'=1.5, average molecular weight=1950, average equivalent weight=980, average functionality=1.99; 15.4 mmoles) were added dropwise via the dropping funnel.

The reaction mixture was heated at 210° C.; polymerization reaction was completed by heating the oil bath up to 250° C. and by distilling away volatiles materials (including BDO) under vacuum (0.01 torr).

After another 2 hours of reaction, the highly viscous reaction mixture was transferred in a mould which was then placed in a press at 250° C. for 8 hours.

The mould was finally cooled at room temperature and the moulded plaque of polymeric material was kept at room temperature for 2 weeks before characterization tests (mechanical testing and superficial characterization) and application runs.

Comparative Example 8

Synthesis of a Fluorinated Polyester from Low Functionality PFPE Diol

Same procedure as in example 7 was repeated but using 30 g of a PFPE mixture of general formula: $Z-O-R_f-Y$ (I) prepared according to the teachings of U.S. Pat. No. 5,262,057, having an average molecular weight of 1900, an average equivalent weight of 1010 and an average functionality of 1.88 (15.8 mmoles).

Comparative Example 9

Synthesis of a Hydrogenated Polyester from a Hydrogenated Diol

Same procedure as in example 7 was repeated, but with no addition of PFPE compounds comprising hydroxyl groups.

Example 10

Extraction Tests

The polymer materials of examples 1., 2., 4., 5., 7. and 8. were submitted to selective extraction. The Applicant has found that these selective extraction conditions are well-suited for miming body fluids extractions.

5 g of the thermoplastic elastomer obtained in each of above mentioned examples was mixed with 50 ml of a mixture dimethylformamide (DMF)/tetrahydrofuran (THF) (DMF/THF=1/9 v/v) at 50° C., as to obtain a slightly opalescent solution at room temperature.

CFC113 was then slowly added; at the beginning of the addition, the solutions became clear; afterwards, further addition caused the polymer to be precipitated. Precipitation of the thermoplastic elastomers was found to be complete once 200 ml of fluorinated non-solvent were added.

The solid fraction was then separated by filtration; the organic phase was washed with water to remove DMF, treated with $Na_2SO_4$ and submitted to fractional distillation in order to remove THF and part of the CFC 113.

The concentrated CFC 113 solution was analyzed by $^{19}$F-NMR in order to provide evidence of the presence of fluorinated extractable residues.

The polymers of example 1., 4., and 7., submitted to the above-described process of extraction, when analyzed by $^{19}$F-NMR, did not provide evidence of the presence of fluorinated extractable residues in the fluorinated non solvent (CFC 113).

The products of example 2., 5. and 8., submitted to analogous extraction processes, showed evidence the presence of 30 mg, 32 mg and 25 mg, respectively, of fluorinated extractable residues. Analysis by $^{19}$F-NMR and $^{1}$H-NMR demonstrated that these fluorinated extractable residues comprised a mixture of non-functional perfluoropolyether derivatives and of oligomers of low average molecular weight and high fluorine content.

Example 11

In Vitro Thrombogenicity Tests

In vitro thrombogenicity tests have been carried out on thin films of thermoplastic elastomers obtained in examples by measuring the activation of prekallikrein (PKK) to kallikrein (KK) as described in Non Patent Citation 0004: SBARBATI DEL GUERRA, R. In vitro biocompatibility of fluorinated polyurethanes. *Journal of Materials Science: Materials in Medicine*, 199 June vol. 5, no. 6-7, p. 452-456. by the proteolytic reaction between KK and the chromogenic substrate H-D-Pro-Phe-Arg-pNa (S-2302 Kabi Diagnostica, Kabi Vitrum, Sweden).

The plasma PKK activation induced by thermoplastic elastomers synthesized in examples 1, 4 and 7 was compared to that induced by the corresponding non-fluorinated counterparts, synthesized according to the procedures described respectively in examples 3, 6 and 9.

The following Table 1 summarizes the results obtained in such in vitro thrombogenicity tests and in references tests carried out with glass (considered as a material highly thrombogenic, i.e. strongly activating the thrombi); silicone (considered in the art as a reference material possessing low thrombogenic activity) and Cardiothane® polyurethane, state-of-the-art material for medical prostheses (see Non Patent Citation 0005: SZYCHER, M. *Blood compatible materials and devices*. SHARMA, C. P. Lancaster, USA: Technomic Publishing Co, 1991.).

It can be observed that thermoplastic elastomers according to the invention possess a thrombogenicity activation factor (KLA) significantly inferior with respect to corresponding hydrogenated counterparts, but also with respect to silicone reference and commercial Cardiothane® material.

TABLE 1

| material | KLA (U/l) |
|---|---|
| glass | 1100 |
| silicone | 820 |
| Cardiothane ® polyurethane | 800 |
| Polymer 1. | 690 |
| Polymer 3. | 810 |
| Polymer 4. | 600 |
| Polymer 6. | 780 |
| Polymer 7. | 650 |
| Polymer 9. | 790 |

The invention claimed is:

1. A process for the manufacture of a medical implant, said process comprising:

reacting a mixture of non functional perfluoropolyethers, monofunctional perfluoropolyethers comprising hydroxyl terminal groups, and bifunctional perfluoropolyethers comprising hydroxyl terminal groups, wherein the average functionality is at least 1.97, mixture (M), with suitable reactants to produce a thermoplastic elastomer; and moulding the so-obtained thermoplastic elastomer to yield at least a part of the medical implant, wherein said mixture (M) consists essentially of perfluoropolyethers complying with formula (I) below:

$$Z-O-R_f-Y \qquad \text{formula (I)}$$

wherein:

$R_f$ is a fluoropolyoxyalkene chain comprising repeating units R°, said repeating units, randomly distributed along the fluoropolyoxyalkene chain, being selected from the group consisting of:

(i) —CFXO—, wherein X is F or $CF_3$, (ii) —$CF_2$CFXO—, wherein X is F or $CF_3$, (iii) —$CF_2CF_2CF_2O$—, and (iv) —$CF_2CF_2CF_2CF_2O$—;

and wherein:

Z and Y, equal to or different from each other are, at each occurrence, independently chosen among:

non functional groups of formula —$CF_3$, —$CF_2CF_3$, —$CF_2CF_2CF_3$, —$(CF_2)_f$—$CF_2(T_1)$, or —$(CF_2)_f$—$CF(T_1)(T_2)$, wherein f is 0 or 1, and wherein $T_1$ and $T_2$, equal to or different from each other, are at each occurrence independently chosen among Cl, Br and H; and functional hydroxyl groups of formula —$CF_2CH_2O$ $(CH_2CH_2O)_{s'}H$ or —$CF_2CF_2CH_2O(CH_2CH_2O)_{s''}H$, wherein s' and s", equal to or different from each other and at each occurrence, are integers from 0 to 5, and wherein the thermoplastic elastomer is selected from the group consisting of a polyurethane comprising:
at least one fluorinated soft block comprising a fluoropolyoxyalkene chain ($R_f$), and
at least one stiff block comprising an hydrocarbon chain ($R_{HC}$) having from 2 to 14 carbon atoms, optionally comprising one or more aromatic or cycloaliphatic group;
said blocks being linked by urethane moieties of formula (II):

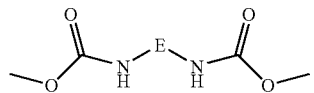

wherein E is a divalent hydrocarbon carbon group, linear or branched, optionally comprising aromatic rings, optionally fluorinated, and a polyester comprising:
at least one fluorinated soft block comprising a fluoropolyoxyalkene chain ($R_f$), and
at least one stiff block comprising an hydrocarbon chain ($R_{HC''}$) having from 2 to 16 carbon atoms, optionally comprising one or more aromatic group;
said blocks being linked by ester moieties of formula (VIII):

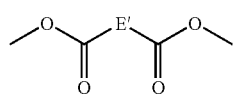

formula (VIII)

wherein E' is a divalent hydrocarbon carbon group, linear or branched, optionally comprising aromatic rings, optionally fluorinated.

2. The process of claim 1, wherein the medical implant is selected from the group consisting of a blood vessel prosthesis, a cardiac surgery device, an angioplastic device, an intraluminal prosthesis for body passageways other than blood vessels, an infusion therapy device, a haemodialysis implant device, a wound dressing device, and an orthopaedic prosthesis.

3. The process according to claim 1, wherein the mixture (M) complies with formula:

$$Z'-CF_2O(CF_2CF_2O)_m-(CF_2O)_n-CF_2-Y',$$

wherein Z' and Y', equal to or different from each other, are, at each occurrence, independently selected from the group consisting of:
neutral groups of formula:
—F, —$CF_3$, —$CF_2CF_3$, Cl, —Br, —H, —$CF_2(T_1)$, or —$CF(T_1)(T_2)$, wherein $T_1$ and $T_2$, equal to or different from each other, are at each occurrence independently chosen among Cl, Br and H; and
functional hydroxyl groups of formula:
—$CH_2(OCH_2CH_2)_{s'''}OH$, wherein s''' has an average value of 1.0 to 3.0, and
wherein m and n are chosen so as to have a m/n ratio of 0.5 to 5 and an average molecular weight of the mixture (M) of from 400 to 10,000.

4. The process according to claim 3, wherein the average molecular weight of the mixture (M) is from 500 to 5,000.

5. The process according to claim 1, said process comprising reacting the mixture (M) with at least one diisocyanate of formula OCN-E-NCO, and at least one chain extender with a molecular weight of 60 to 450 g/mol selected from the group consisting of diols of formula HO—$R_{HC}$—OH; diamines of formula $H_2N$—$R_{HC}$—$NH_2$; and combinations thereof.

6. The process according to claim 1, wherein the thermoplastic elastomer is a polyurethane further comprising a soft segment comprising a polyoxyalkene chain ($R_{OH}$) complying with formula (III) or (IV) here below:

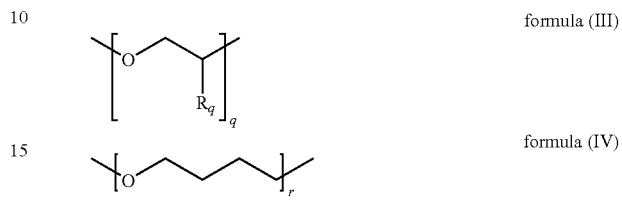

formula (III)

formula (IV)

wherein $R_q$, equal or different at each occurrence, is —H or —$CH_3$; and q and r are, independently, integers from 5 to 250.

7. The process according to claim 6, wherein q and r are, independently, integers from 10 to 125.

8. The process according to claim 1, wherein the thermoplastic elastomer is a polyurethane further comprising a soft segment comprising a polyester chain chosen among formulae (V) to (VII) here below and mixtures thereof:

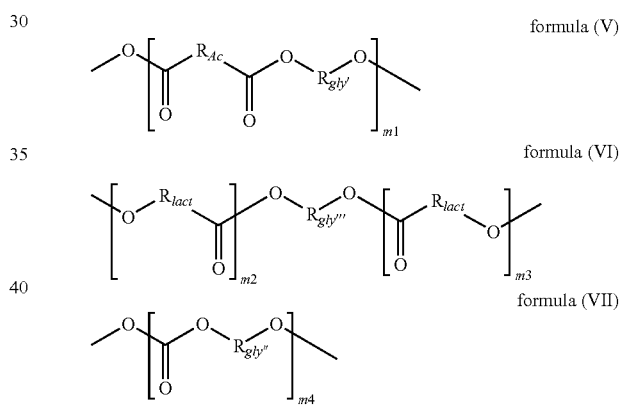

formula (V)

formula (VI)

formula (VII)

wherein:
$R_{AG}$, equal or different at each occurrence, is independently a divalent $C_1$-$C_{12}$ hydrocarbon group, linear or branched, optionally substituted, optionally comprising one or more aromatic rings;
$R_{gly'}$, $R_{gly''}$, $R_{gly'''}$, equal or different at each occurrence, are independently selected among $C_1$-$C_6$ hydrocarbon group;
$R_{lact}$, equal or different at each occurrence, is a $C_2$-$C_{12}$ hydrocarbon group;
wherein $m_1$, $m_2$, $m_3$, $m_4$ are, independently, integers such that the polyester chain has an average molecular weight of from 500 to 5,000.

9. The process according to claim 8, wherein $R_{AC}$ is a —$(CH_2)_{nAc}$—group, and wherein $n_{AC}$ is an integer from 1 to 6.

10. The process according to claim 8, wherein $R_{gly'}$, $R_{gly''}$, $R_{gly'''}$, equal or different at each occurrence, are independently selected from the group of structures consisting of:
—$(CH_2)_2$—; —$(CH_2)_4$—; —$(CH_2)_6$—; —$CH(CH_3)$—$CH_2$—; and —$CH_2$—$C(CH_3)_2$—$CH_2$—.

11. The process according to claim 8, wherein $R_{lact}$ is a —$(CH_2)_5$—group.

12. The process according to claim 8, wherein $m_1$, $m_2$, $m_3$, $m_4$ are, independently, integers such that the polyester chain has an average molecular weight of from 500 to 2,000.

13. The process according to the claim 1, said process comprising reacting the mixture (M) with at least one diacid of formula HOOC-E'-COOH, and at least one diol of formula HO—$R_{HC'}$—OH.

14. The process according to claim 1, wherein said repeating units $R°$, is selected from the group consisting of:
 (i) —CFXO—, wherein X is F or $CF_3$, and
 (ii) —$CF_2$CFXO—,
 wherein X is F or $CF_3$.

15. The process according to claim 1, wherein the hydrocarbon chain ($R_{HC}$) is selected from the group consisting of: ethanediol, 1,4-butanediol, 1,6-hexanediol, diethylene glycol, dipropylene glycol, isophoronediamine, ethylene diamine, 1,2-propylenediamine, 1,3-propylenediamine, N-methyl-propylene-1,3-diamine, and N,N'-dimethylethylenediamine.

* * * * *